(12) United States Patent
Takahashi et al.

(10) Patent No.: US 10,048,343 B2
(45) Date of Patent: Aug. 14, 2018

(54) MAGNETIC RESONANCE IMAGING APPARATUS AND MAGNETIC RESONANCE IMAGING METHOD

(71) Applicant: HITACHI, LTD., Tokyo (JP)

(72) Inventors: Miyuki Takahashi, Tokyo (JP); Hikaru Hanada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 360 days.

(21) Appl. No.: 14/785,454

(22) PCT Filed: May 8, 2014

(86) PCT No.: PCT/JP2014/062306
§ 371 (c)(1),
(2) Date: Oct. 19, 2015

(87) PCT Pub. No.: WO2014/185323
PCT Pub. Date: Nov. 20, 2014

(65) Prior Publication Data
US 2016/0054415 A1  Feb. 25, 2016

(30) Foreign Application Priority Data

May 17, 2013 (JP) ................. 2013-104955

(51) Int. Cl.
*G01V 3/00* (2006.01)
*G01R 33/56* (2006.01)
(Continued)

(52) U.S. Cl.
CPC .............. *G01R 33/56* (2013.01); *A61B 5/055* (2013.01); *G01R 33/4824* (2013.01);
(Continued)

(58) Field of Classification Search
CPC .. G01R 33/56; G01R 33/4824; G01R 33/565; G01R 33/56509; G01R 33/56563; G01R 33/56572; A61B 5/055
(Continued)

(56) References Cited

U.S. PATENT DOCUMENTS 6,188,219 B1 * 2/2001 Reeder ................... G01R 33/58
324/307
7,023,207 B1 * 4/2006 Gaddipati .......... G01R 33/4824
324/307
(Continued)

FOREIGN PATENT DOCUMENTS

JP       2005-21691         1/2005
WO    WO2005/023108 A1   3/2005
(Continued)

OTHER PUBLICATIONS

International Search Report in PCT/JP2014/062306.

*Primary Examiner* — Jermele M Hollington
*Assistant Examiner* — Sean Curtis
(74) *Attorney, Agent, or Firm* — Cooper & Dunham LLP

(57) ABSTRACT

It is an object of the present invention to provide a technique for reducing the degradation of the image quality due to the phase difference between scanning trajectories (blades) in measurement using a non-orthogonal sampling method. Therefore, in the present invention, correction for reducing the phase difference between a plurality of scanning trajectories (blades) measured by using a non-orthogonal sampling method is performed at the time of image reconstruction. For example, the reduction of the phase difference is performed using a method of matching the phases at the intersections between blades, matching the phases of all blades at positions determined by considering the shift
(Continued)

amount in the frequency direction, or canceling out the phase change amount of each blade obtained by calculation.

12 Claims, 10 Drawing Sheets

(51) Int. Cl.
  *A61B 5/055*   (2006.01)
  *G01R 33/48*   (2006.01)
  *G01R 33/565*   (2006.01)

(52) U.S. Cl.
  CPC ...... *G01R 33/565* (2013.01); *G01R 33/56509* (2013.01); *G01R 33/56563* (2013.01); *G01R 33/56572* (2013.01)

(58) Field of Classification Search
  USPC ................................. 324/300–322
  See application file for complete search history.

(56) References Cited

U.S. PATENT DOCUMENTS

| | | | | |
|---|---|---|---|---|
| 7,279,892 B2* | 10/2007 | Speier | ............... | G01R 33/4824 324/307 |
| 7,382,127 B2* | 6/2008 | Gaddipati | .......... | G01R 33/4824 324/307 |
| 7,482,806 B2* | 1/2009 | Stemmer | ............ | G01R 33/4824 324/307 |
| 7,786,728 B2* | 8/2010 | Fukuta | ................. | G01R 33/561 324/307 |
| 7,840,049 B2* | 11/2010 | Stemmer | ............. | G01R 33/561 324/309 |
| 7,847,546 B2* | 12/2010 | Takizawa | ........... | G01R 33/4824 324/307 |
| 8,082,127 B2* | 12/2011 | Ruhm | ................. | G01R 33/4824 324/300 |
| 8,154,294 B2* | 4/2012 | Takizawa | ............. | G01R 33/482 324/309 |
| 8,344,729 B2* | 1/2013 | Takizawa | ........... | G01R 33/4824 324/307 |
| 9,064,303 B2* | 6/2015 | Kawamura | .......... | A61B 5/7207 |
| 9,234,953 B2* | 1/2016 | Labadie | ............. | G01R 33/4818 |
| 9,341,694 B2* | 5/2016 | Pfeuffer | ................. | A61B 5/055 |
| 9,476,955 B2* | 10/2016 | Stemmer | ................ | G01R 33/543 |
| 9,535,146 B2* | 1/2017 | Kamada | ............ | G01R 33/4824 |
| 2005/0004448 A1 | 1/2005 | Gurr et al. | | |
| 2006/0253018 A1* | 11/2006 | Speier | ................ | G01R 33/4824 600/410 |
| 2006/0264735 A1* | 11/2006 | Stemmer | ............ | G01R 33/4824 600/410 |
| 2008/0068016 A1* | 3/2008 | Gaddipati | .......... | G01R 33/4824 324/318 |
| 2008/0129289 A1* | 6/2008 | Stemmer | ............ | G01R 33/4824 324/309 |
| 2009/0115794 A1* | 5/2009 | Fukuta | ................. | G01R 33/561 345/581 |
| 2010/0141253 A1* | 6/2010 | Takizawa | ........... | G01R 33/4824 324/309 |
| 2010/0164495 A1 | 7/2010 | Takizawa et al. | | |
| 2010/0286500 A1* | 11/2010 | Ruhm | ................ | G01R 33/4824 600/410 |
| 2010/0296717 A1 | 11/2010 | Takizawa | | |
| 2011/0089948 A1* | 4/2011 | Takizawa | ........... | G01R 33/4824 324/309 |
| 2012/0313640 A1* | 12/2012 | Pfeuffer | ................. | A61B 5/055 324/309 |
| 2012/0313641 A1* | 12/2012 | Labadie | ............. | G01R 33/4818 324/309 |
| 2013/0170727 A1* | 7/2013 | Kawamura | .......... | A61B 5/7207 382/131 |
| 2013/0249548 A1* | 9/2013 | Stemmer | ............ | G01R 33/4835 324/309 |
| 2014/0197835 A1* | 7/2014 | Kamada | ............ | G01R 33/4824 324/309 |
| 2016/0054415 A1* | 2/2016 | Takahashi | .............. | A61B 5/055 324/318 |

FOREIGN PATENT DOCUMENTS

| | | |
|---|---|---|
| WO | WO2007/013423 A1 | 2/2007 |
| WO | WO2008/152937 A1 | 12/2008 |
| WO | WO2009/093517 A1 | 7/2009 |

* cited by examiner

FIG.3
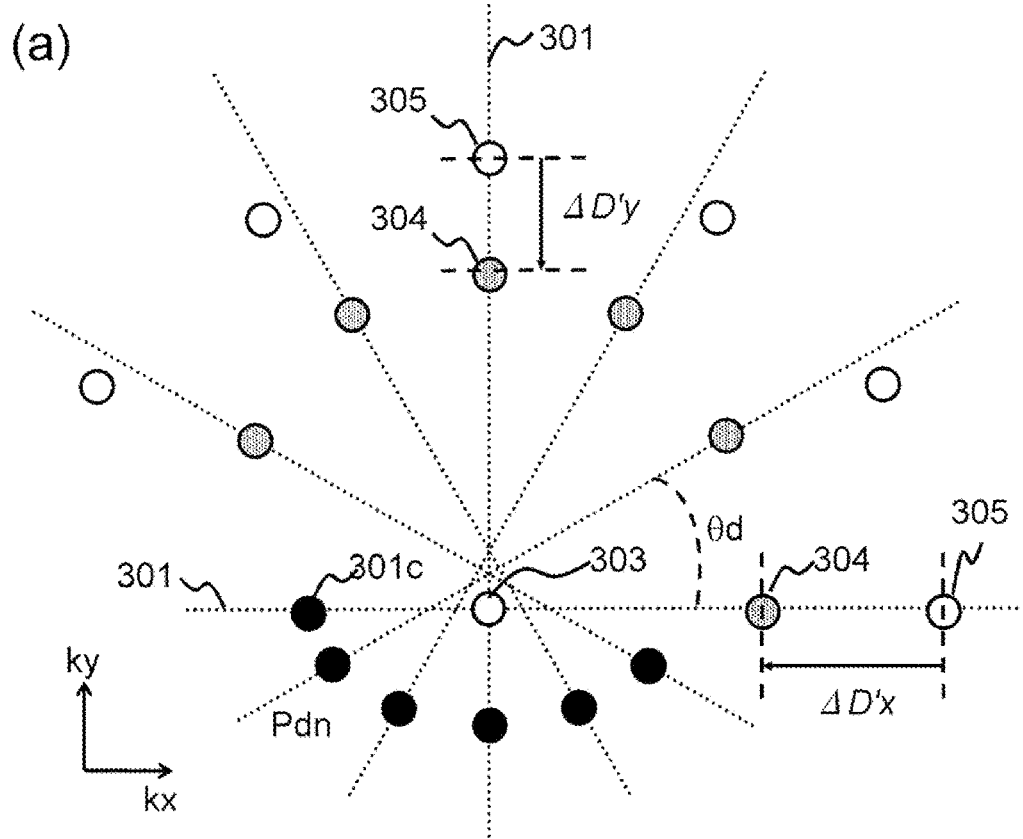
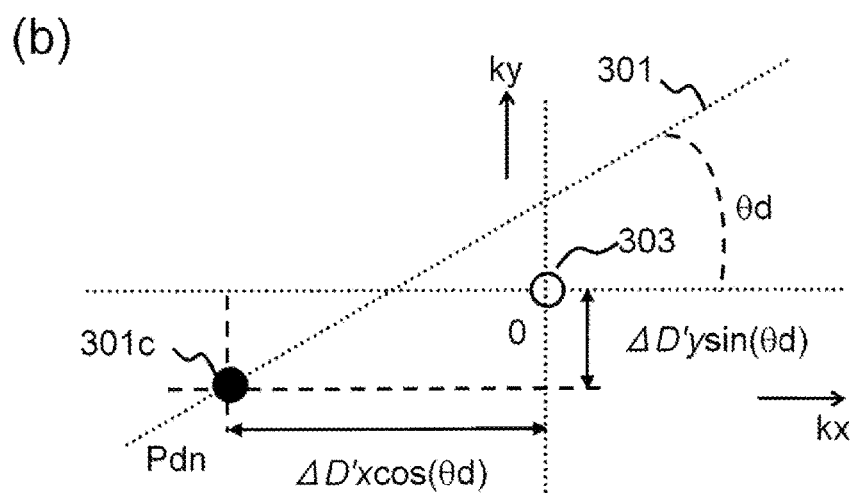

FIG.4
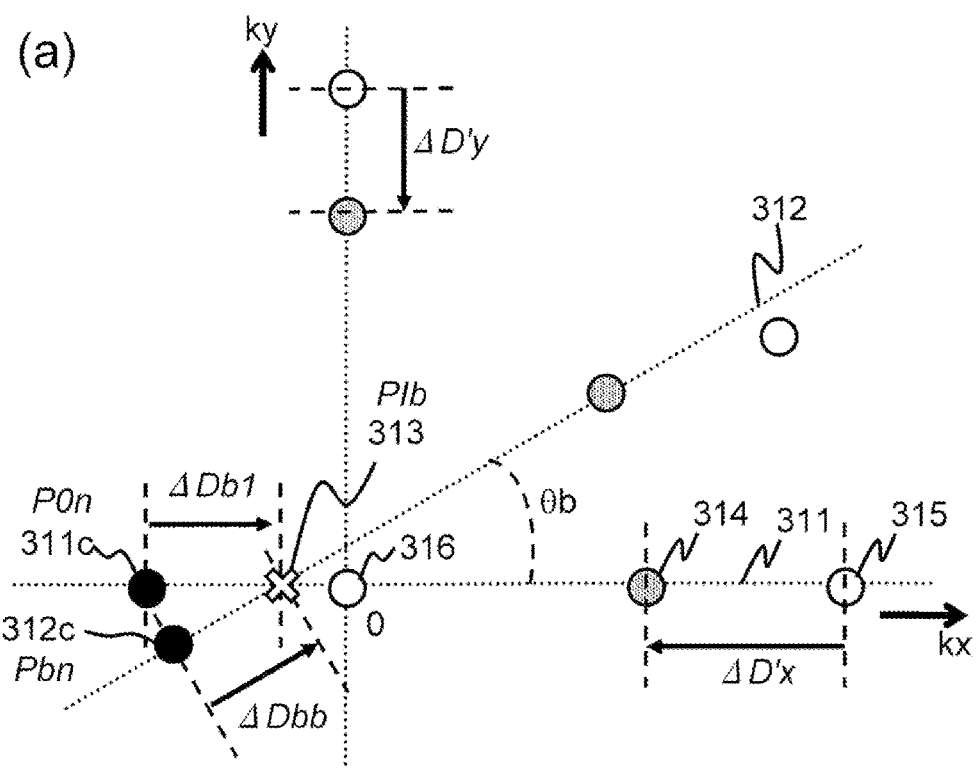
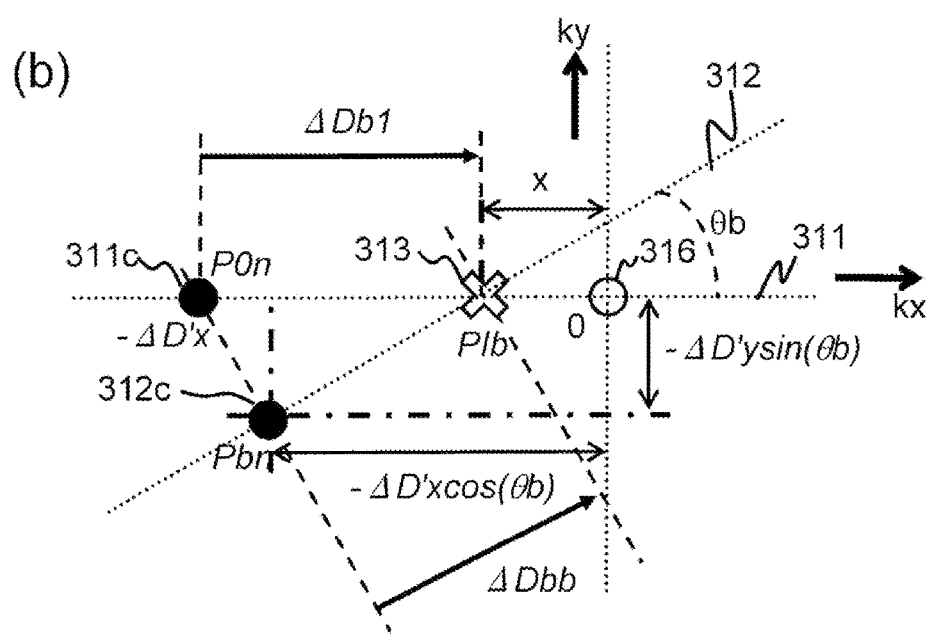

FIG.7
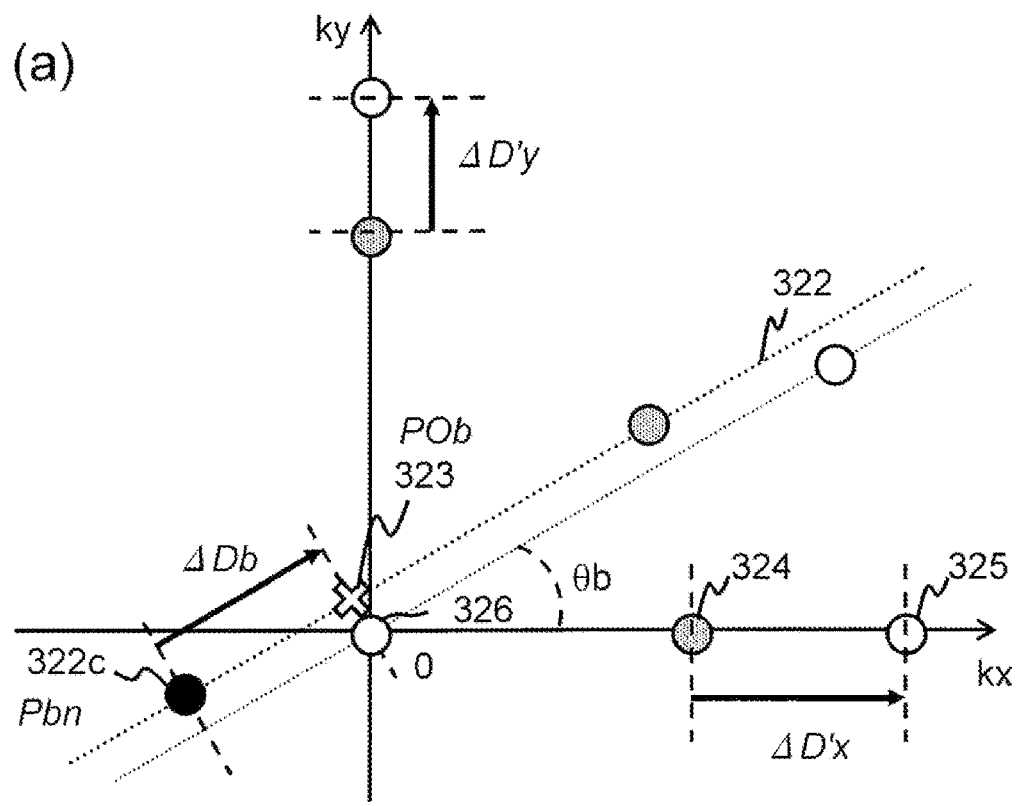
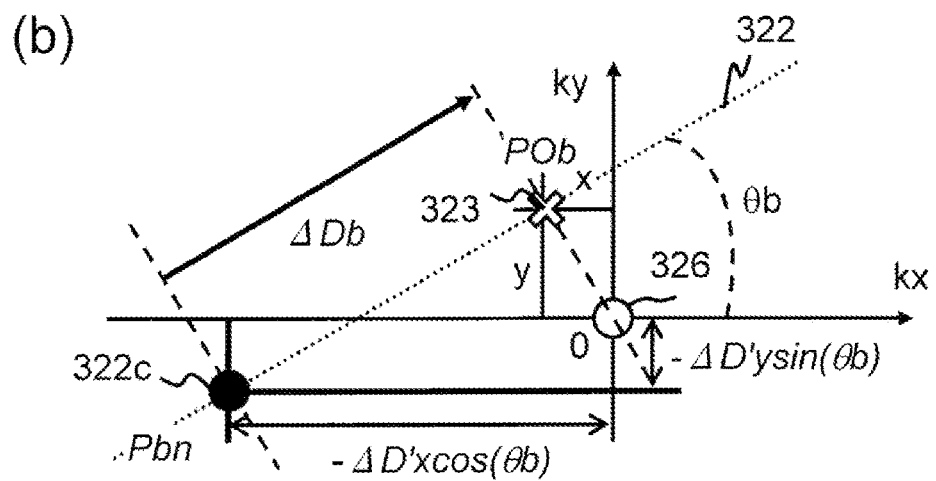

MAGNETIC RESONANCE IMAGING APPARATUS AND MAGNETIC RESONANCE IMAGING METHOD

TECHNICAL FIELD

The present invention relates to a magnetic resonance imaging (hereinafter, referred to as "MRI") technique, and in particular, to an MRI technique using a non-orthogonal sampling method.

BACKGROUND ART

The MRI apparatus is an apparatus that measures an NMR signal generated by an object, especially, the spins of nuclei that form human tissue, and images the shapes or functions of the head, abdomen, limbs, and the like in a two-dimensional manner or in a three-dimensional manner. In the imaging, according to a sequence set in advance, NMR signals having been subjected to different phase encoding and frequency encoding by the gradient magnetic field are measured as time series data. Then, the measured NMR signals are reconstructed as an image by a two-dimensional or three-dimensional Fourier transform.

In the non-orthogonal sampling method, such as a radial sampling method or a hybrid radial method, data required for reconstructing one image is obtained by performing sampling by radially scanning the measurement space at various rotation angles with approximately one point (generally, the origin) of the measurement space as the rotation center. It is known that radial sampling is resistant to artifacts due to body motion. However, scanning trajectories (blades) overlap each other in the measurement space. For this reason, if the positional relationship between the blades is not appropriate or the phase difference at the intersection between the blades occurs, the image quality of the reconstructed image is degraded.

Hereinafter, in this specification, one straight trajectory in the radial sampling method and a plurality of parallel straight trajectories in the hybrid radial method will be referred to collectively as a blade.

However, in the actual imaging, due to non-uniformity of the static magnetic field or the output error of the gradient magnetic field, the arrangement position of each blade in the measurement space is different from the calculated arrangement position (coordinates) or a phase difference occurs at the intersection between the blades. As a technique for correcting the error of the arrangement position of the blade, there is a method of acquiring data for calculating the shift amount of the blade position caused by the output error of the gradient magnetic field, calculating the shift amount of each blade on the k-space, and correcting the error of the arrangement position of each blade during the image reconstruction processing (for example, refer to PTL 1).

CITATION LIST

Patent Literature

[PTL 1] Pamphlet of International Publication No. 2008/152937
[PTL 2] Japanese Unexamined Patent Application Publication No. 2005-152175

SUMMARY OF INVENTION

Technical Problem

In the technique disclosed in PTL 1, however, the phase difference at the intersection between the blades is not corrected. When there is a phase difference in a place where the blades overlap each other in the measurement space, signals are canceled out. Accordingly, pixel value unevenness or degradation of image formation occurs in the image.

The present invention has been made in view of the aforementioned situation, and it is an object of the present invention to provide a technique for reducing the degradation of the image quality due to the phase difference at the intersection between scanning trajectories (blades) in measurement using a non-orthogonal sampling method.

Solution to Problem

In the present invention, correction for reducing the phase difference at the intersection between a plurality of scanning trajectories (blades) measured by using a non-orthogonal sampling method is performed at the time of image reconstruction. For example, the reduction of the phase difference is performed using a method of matching the phases at the intersections between blades, matching the phases of all blades at positions determined by considering the shift amount in the frequency direction, or canceling out the phase change amount of each blade obtained by calculation.

Advantageous Effects of Invention

According to the present invention, in the measurement using a non-orthogonal sampling method, it is possible to reduce the degradation of the image quality due to the phase difference between the scanning trajectories (blades).

BRIEF DESCRIPTION OF DRAWINGS

FIG. 3(a) is a diagram for explaining the peak shift of an echo signal in the first embodiment, and FIG. 3(b) is an enlarged view of the vicinity of a k-space origin in FIG. 3(a).

FIG. 4(a) is a diagram for explaining a phase correction amount calculation method of the first embodiment, and FIG. 4(b) is an enlarged view of the vicinity of the k-space origin in FIG. 4(a).

FIG. 7(a) is a diagram for explaining a phase correction amount calculation method of a second embodiment, and FIG. 7(b) is an enlarged view of the vicinity of a k-space origin in FIG. 7(a).

DESCRIPTION OF EMBODIMENTS

<<First Embodiment>>

Figure 1:
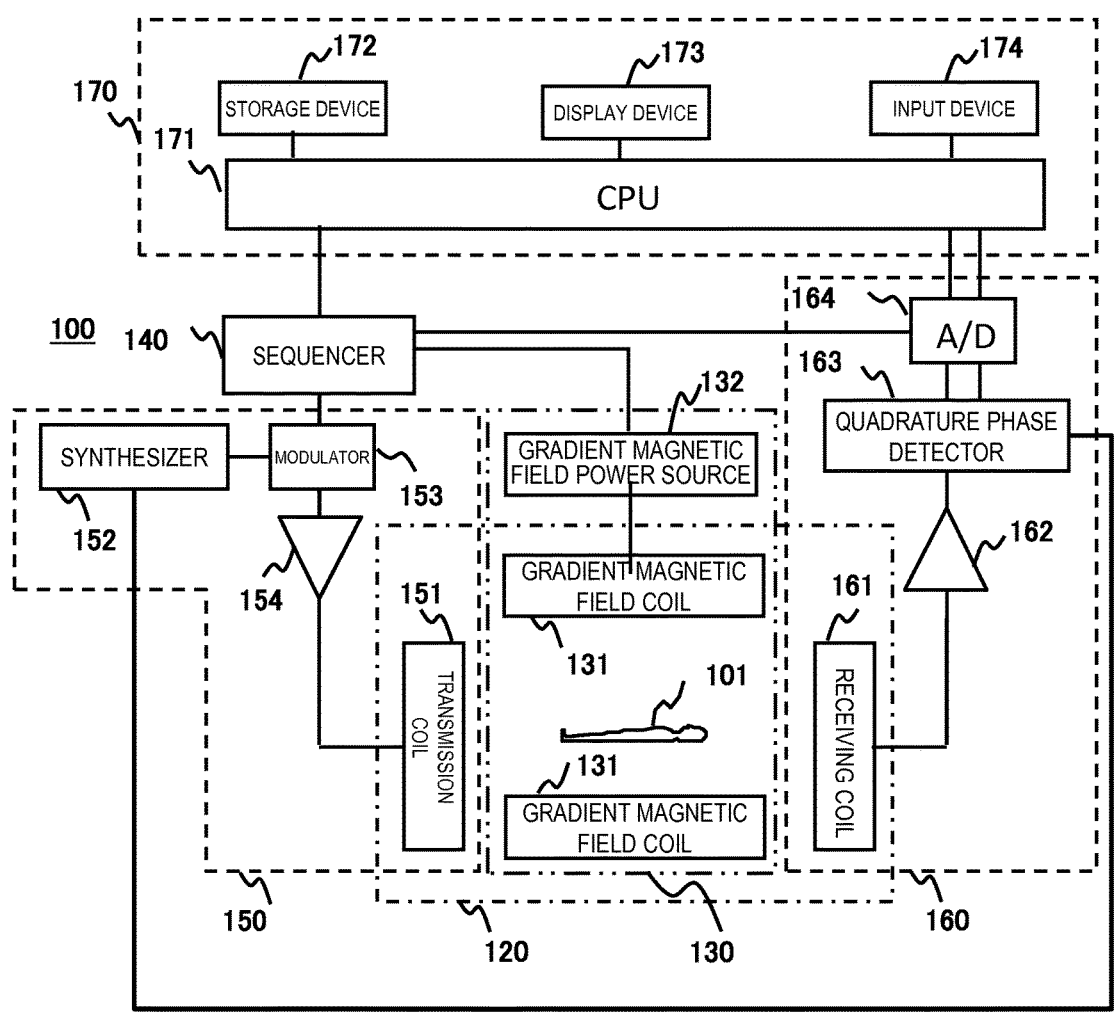
FIG. 1 is a block diagram showing the overall configuration of a magnetic resonance imaging apparatus of a first embodiment.

Hereinafter, preferred embodiments of the present invention will be described in detail with reference to the accompanying diagrams. In all diagrams for explaining the embodiments of the invention, the same reference numerals are given to components having the same functions unless otherwise stated, and repeated explanation thereof will be omitted.

First, the overall outline of an example of an MRI apparatus of the present embodiment will be described with reference to FIG. 1. FIG. 1 is a block diagram showing the overall configuration of an embodiment of the MRI apparatus of the present embodiment.

An MRI apparatus 100 of the present embodiment acquires a tomographic image of an object using an NMR phenomenon. As shown in FIG. 1, the MRI apparatus 100 includes a static magnetic field generation unit 120, a gradient magnetic field generation unit 130, a high frequency magnetic field generation unit (hereinafter, a transmission unit) 150, a high frequency magnetic field detection unit (hereinafter, a receiving unit) 160, a control processing unit 170, and a sequencer 140.

The static magnetic field generation unit 120 generates a uniform static magnetic field in a space around an object 101 in a direction perpendicular to the body axis in the case of a vertical magnetic field method and in the body axis direction in the case of a horizontal magnetic field method, and includes a permanent magnet type, normal conduction type, or superconducting type static magnetic field generator disposed around the object 101.

The gradient magnetic field generation unit 130 includes gradient magnetic field coils 131 wound in three axial directions of X, Y, and Z, which are the coordinate system (device coordinate system) of the MRI apparatus 100, and a gradient magnetic field power source 132 for driving each of the gradient magnetic field coils, and applies gradient magnetic fields Gx, Gy, and Gz in the three axial directions of X, Y, and Z by driving the gradient magnetic field power source 132 of each gradient magnetic field coil 131 according to a command from the sequencer 140, which will be described later.

The transmission unit 150 emits a high frequency magnetic field pulse (hereinafter, referred to as an "RF pulse") to the object 101 in order to cause nuclear magnetic resonance in the nuclear spins of atoms that form the body tissue of the object 101, and includes a high frequency oscillator (synthesizer) 152, a modulator 153, a high frequency amplifier 154, and a transmission-side high frequency coil (transmission coil) 151. The high frequency oscillator 152 generates an RF pulse. The modulator 153 performs amplitude modulation of the output RF pulse according to the command from the sequencer 140. The high frequency amplifier 154 amplifies the amplitude-modulated RF pulse, and supplies the amplified RF pulse to the transmission coil 151 disposed near the object 101. The transmission coil 151 emits the supplied RF pulse to the object 101.

The receiving unit 160 detects a nuclear magnetic resonance signal (an echo signal, an NMR signal) emitted by the nuclear magnetic resonance of the nuclear spins that form the body tissue of the object 101, and includes a receiving-side high frequency coil (receiving coil) 161, a signal amplifier 162, a quadrature phase detector 163, and an A/D converter 164. The receiving coil 161 is disposed near the object 101, and detects an NMR signal of the response from the object 101 that is induced by the electromagnetic wave emitted from the transmission coil 151. The detected NMR signal is amplified by the signal amplifier 162 and is then divided into two orthogonal signals by the quadrature phase detector 163 at a timing according to the command from the sequencer 140. Each of the orthogonal signals is converted into the digital amount by the A/D converter 164 and is transmitted to the control processing unit 170.

The sequencer 140 applies an RF pulse and a gradient magnetic field pulse according to an instruction from the control processing unit 170. Specifically, the sequencer 140 transmits various commands, which are required for the data collection of a tomographic image of the object 101, to the transmission unit 150, the gradient magnetic field generation unit 130, and the receiving unit 160 according to the instruction from the control processing unit 170.

The control processing unit 170 performs overall control of the MRI apparatus 100, operations of various kinds of data processing, display and storage of processing results, and the like, and includes a CPU 171, a storage device 172, a display device 173, and an input device 174. The storage device 172 is formed by an internal storage device, such as a hard disk, and an external storage device, such as an external hard disk, an optical disc, and a magnetic disk. The display device 173 is a CRT, a liquid crystal display device, or the like. The input device 174 is an interface for the input of various kinds of control information of the MRI apparatus 100 or control information of processing performed in the control processing unit 170. For example, the input device 74 includes a track ball, a mouse, and a keyboard. The input device 174 is disposed near the display device 173. An operator interactively inputs instructions and data, which are required for the various kinds of processing of the MRI apparatus 100, through the input device 174 while observing the display device 173.

The CPU 171 realizes the control of the operation of the MRI apparatus 100 and each process of the control processing unit 170, such as various kinds of data processing, by executing a program stored in advance in the storage device 172 according to the instruction input by the operator. The command to the sequencer 140 is performed according to the pulse sequence stored in advance in the storage device 172. For example, when data from the receiving unit 160 is input to the control processing unit 170, the CPU 171 executes signal processing, image reconstruction processing, and the like, and displays a tomographic image of the object 101, which is the result, on the display device 173 and stores the tomographic image in the storage device 172.

The transmission coil 151 and the gradient magnetic field coil 131 are provided in the static magnetic field space of the static magnetic field generation unit 120, into which the object 101 is inserted, so as to face the object 101 in the case of a vertical magnetic field method and so as to surround the object 101 in the case of a horizontal magnetic field method. In addition, the receiving coil 161 is provided so as to face or surround the object 101.

Currently, nuclides imaged by the MRI apparatus, which are widely used clinically, include a hydrogen nucleus (proton) that is a main constituent material of the object 101. In the MRI apparatus 100, the shapes or functions of the head, abdomen, limbs, and the like of the human body are imaged in a two-dimensional or three-dimensional manner by imaging the spatial distribution of the proton density or the information regarding the spatial distribution of the relaxation time of the excited state.

Figure 2:
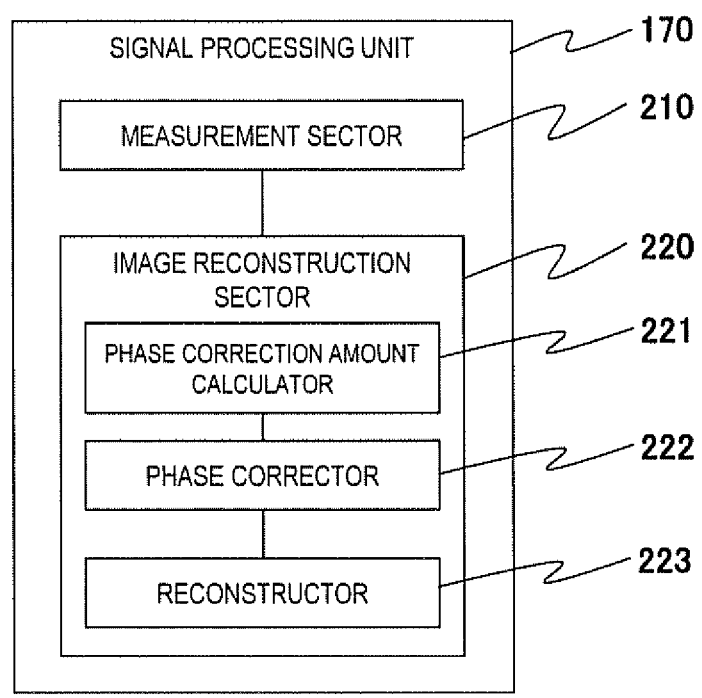
FIG. 2 is a functional block diagram of a control processing system of the first embodiment.

As shown in FIG. 2, the control processing unit 170 of the present embodiment includes a measurement sector 210, which measures echo signals along a plurality of scanning trajectories of a predetermined measurement space (k-space) according to the pulse sequence of the non-orthogonal sampling method and arranges the echo signals on the scanning trajectories as data streams, and an image reconstruction sector 220 that reconstructs an image from the plurality of echo signals to obtain a reconstructed image.

The measurement sector 210 controls the operations of the static magnetic field generation unit 120, the gradient magnetic field generation unit 130, the high frequency magnetic field generation unit 150, and the high frequency magnetic field detection unit 160 according to the pulse sequence of the non-orthogonal sampling method, and arranges data streams, which are obtained by sampling the echo signals, on the scanning trajectories of the k-space. In the present embodiment, each scanning trajectory will be referred to hereinafter as a blade.

In addition, the image reconstruction sector 220 obtains a reconstructed image by reducing the phase difference in the low spatial frequency region between the data streams on the respective blades of the k-space. In order to realize this, the image reconstruction sector 220 of the present embodiment includes a phase correction amount calculator 221 that calculates the correction amount of the phase (phase correction amount) of each data stream on a plurality of blades, a phase corrector 222 that corrects the phase of each data stream on the plurality of blades using the calculated phase correction amount, and a reconstructor 223 that calculates a reconstructed image from the data streams on the plurality of blades after the correction. The phase correction amount calculated by the phase correction amount calculator 221 is calculated so as to reduce the phase difference between the data streams on the plurality of blades.

The phase correction amount calculator 221 calculates the phase correction amount so that the phases of data at a predetermined position on the blades in a plurality of data streams match each other. In this case, the predetermined position is determined so as to reflect a peak shift amount that is the shift amount of the center (peak position) of the echo signals from the k-space origin.

In the present embodiment, the predetermined position is assumed to be an intersection of the plurality of blades. Specifically, assuming that the predetermined position is an intersection between a blade as a reference (reference blade) set in advance among the plurality of blades and a blade other than the reference blade, the phase correction amount calculator 221 calculates the phase correction amount so that the phase at the intersection of the data stream on each blade other than the reference blade matches the phase at the intersection of the data stream on the reference blade.

The phase correction amount calculator 221 of the present embodiment calculates the position of an intersection using the peak shift amount for each data stream on the blade other than the reference blade, calculates a distance from the intersection to the midpoint of the data stream and a distance from the intersection to the midpoint of the data stream (reference data stream) on the reference blade using the information of the calculated position of the intersection, and calculates a phase at the intersection of the data stream and a phase at the intersection of the reference data stream using the calculated distances.

As described above, in the present embodiment, when calculating the phase correction amount, the peak shift amount of the echo signal is used. The peak shift that is a shift of the peak position of the echo signal occurs due to non-uniformity of the static magnetic field and the output error of the gradient magnetic field. In addition, the peak position of the echo signal changes according to the area of the dephase pulse applied before the application of the read gradient magnetic field pulse. This is because the timing, at which the phases of the echo signals match each other by the application of the read gradient magnetic field pulse set in advance by the pulse sequence after dephasing, becomes the peak position.

The shift amount of the echo signal (peak shift amount) is separately calculated by performing a pre-scan or the like in advance. Therefore, it is possible to prevent an increase in the imaging time. For example, the calculation is performed using an echo signal that is acquired by the pulse sequence to acquire only a specific echo signal, for example, as disclosed in PTL 2.

Prior to the detailed explanation of the calculation of the phase correction amount of the present embodiment, the shift of each blade due to the peak shift of the echo signal will be briefly described. In this description, in order to simplify explanation, a case in which the imaging section is an XY plane of the device coordinate system of the MRI apparatus 100 will be described below as an example.

FIG. 3(a) is a diagram for explaining the shift of a blade 301, which is a scanning trajectory, due to the peak shift of the echo signal on the k-space. Here, for the sake of simplicity, a case is shown in which the X and Y axes of the device coordinate system match kx and ky axes of the coordinate system (measurement coordinate system) on the k-space, respectively. Hereinafter, it is assumed that the scanning trajectory in this description is the same in all diagrams illustrated. In this diagram, a position 305 of the circle is a position of data that forms each blade 301 when there is no shift (positional shift) in the blade 301, and a position 304 of the circle is a (actual) data position when there is a shift. For example, if there is no shift, a blade center 301c of the blade 301 disposed on the kx axis is a position 303 of the origin of the k-space. However, since there is a shift, the blade center of the blade 301 is the position of 301c in practice.

In the present embodiment, a value (coordinate value) of coordinates Pdn on the k-space coordinates of the blade center 301c after the shift is calculated as the shift amount of the blade 301. Assuming that the shift amount in the X-axis direction and the shift amount in the Y-axis direction, which are caused by the peak shift that occurs due to the non-uniformity of the static magnetic field, the output error of the gradient magnetic field, or the like described above, are ΔD'x and ΔD'y, the shift amount ΔD'x_d of the d-th (d is an integer of 1 or more) blade 301 in the kx direction and the shift amount ΔD'y_d of the d-th blade 301 in the ky direction are expressed by the following expressions (1) and (2), respectively, as shown in FIG. 3(b).

$$\Delta D'x\_d = \Delta D'x \cos(\theta d) \quad (1)$$

$$\Delta D'y\_d = \Delta D'y \sin(\theta d) \quad (2)$$

Therefore, the coordinates Pdn{x, y} of the d-th blade center 301c on the k-space are expressed by the following expression (3).

$$Pdn\{x,y\} = \{\Delta D'x \cos(\theta d), \Delta D'y \sin(\theta d)\} \quad (3)$$

Here, θd is an angle between the d-th blade 301 and the X axis.

Next, details of the phase correction amount calculation of the phase correction amount calculator 221 of the present embodiment will be described with reference to the diagrams. FIGS. 4(a) and 4(b) are diagrams for explaining a method of calculating the phase correction amount in the present embodiment. FIG. 4(b) is an enlarged view of the vicinity of the k-space center in FIG. 4(a). Here, a first blade 311 is disposed on the kx axis of the k-space, and this is assumed to be the reference blade 311.

The reference blade 311 is not limited to the blade on the kx axis, and any blade may be set as the reference blade 311.

An intersection between a b-th blade (b is an integer of 2 or more) 312 and the reference blade 311 is assumed to be an intersection 313. In this diagram, a position 315 indicated by a circle is an ideal data position when there is no positional shift (shift) in the blade, and a position 314 indicated by a circle is an actual data position reflecting the shift of the blade.

When there is no shift, the b-th blade 312 intersects the reference blade 311 at an origin 316 of the k-space. In practice, however, since there is a shift in each blade, both the blades intersect each other at the position (intersection) 313 indicated by a white cross. In the present embodiment, phase correction is performed so that the phase of the b-th blade 312 at the intersection 313 matches the phase of the reference blade at the intersection 313.

The phase correction amount calculator 221 of the present embodiment calculates the coordinates of the intersection 313, calculates distances $\Delta Db1$ and $\Delta Dbb$ between the intersection 313 and midpoints (blade centers) 311c and 312c of the blades 311 and 312, and calculates the phase values (Phase_1, Phase_b) of the blades 311 and 312 at the intersection 313. Then, a difference (phase difference) between the phase value of the b-th blade 312 at the intersection 313 and the phase value of the reference blade 311 at the intersection 313 is calculated as a phase correction amount PhC_b.

The distances $\Delta Db1$ and $\Delta Dbb$ between the intersection 313 and the blade centers 311c and 312c are calculated from the peak shift amount $\Delta D'x$ in the X-axis direction, the peak shift amount $\Delta D'y$ in the Y-axis direction, and a blade angle $\theta b$ of the b-th blade 312. In the present embodiment, the blade angle $\theta b$ is assumed to be an angle between the b-th blade 312 and the X axis.

From FIG. 4(b) and the above expression (3), coordinates PIb{x, y} of the intersection 313 have the relationship of the following expressions (4) and (5) when expressed using the peak shift amounts $\Delta D'x$ and $\Delta D'y$ and the blade angle $\theta b$.

$$y+\Delta D'y \sin(\theta b)=\tan(\theta b)\{x+\Delta D'x \cos(\theta b)\} \quad (4)$$

$$y=0 \quad (5)$$

Therefore, the coordinates PIb{x, y} of the intersection 313 are expressed by the following expression (6) using the peak shift amount and the blade angle $\theta b$ of the b-th blade 312.

$$PIb\{x,y\}=\{\cos(\theta b)\cdot(\Delta D'y-\Delta D'x),0\} \quad (6)$$

Using the coordinate value of the intersection 313, the distance $\Delta Db1$ from the midpoint 311c of the reference blade 311 to the intersection 313 and the distance $\Delta Dbb$ from the midpoint 312c of the b-th blade 312 to the intersection 313 are calculated by the following expressions (7), (8), and (9).

$$\Delta Db1=\Delta D'x\{1-\cos(\theta b)\}+\Delta D'y \cos(\theta b) \quad (7)$$

$$\Delta Dbb=\Delta D'y \quad (8)$$

$$\therefore |\Delta Dbb|^2=[\cos(\theta b)\cdot(\Delta D'y-\Delta D'x)+\Delta D'x \cos(\theta b)]^2+ [\Delta D'y \sin(\theta b)]^2=(\Delta D'y)^2 \quad (9)$$

Then, real and imaginary signal values at the calculated position of the intersection 313 are acquired by interpolation, and the phase value Phase_1 of the reference blade 311 at the intersection 313 and the phase value Phase_b of the b-th blade 312 at the intersection 313 are obtained according to the following expressions (10) and (11).

$$\text{Phase\_1}=\tan^{-1}(\text{Blade\_1}(\text{Imaginary}(\text{CENTER}+\Delta Db1))/\text{Blade\_1}(\text{Real}(N/2+\Delta Db1))) \quad (10)$$

$$\text{Phase\_b}=\tan^{-1}(\text{Blade\_b}(\text{Imaginary}(\text{CENTER}+\Delta Dbb))/\text{Blade\_b}(\text{Real}(N/2+\Delta Dbb))) \quad (11)$$

Here, Blade_1 ( ) and Blade_b_( ) indicate data streams of the reference blade 311 and the b-th blade 312, respectively. Real( ) indicates real part data, Imaginary( ) indicates imaginary part data, N indicates the number of data points of each blade, and CENTER indicates the position of each of the midpoints 311c and 312c.

Therefore, the phase correction amount (phase difference) PhC_b is obtained by the following expression (12).

$$\text{PhC\_b}=\text{Phase\_b}-\text{Phase\_1} \quad (12)$$

By applying the phase correction amount PhC_b to the data stream of the b-th blade 312 and correcting the phase value, the phase value of the first blade 311 at the intersection 313 matches the phase value of the b-th blade 312 at the intersection 313.

Figure 5:
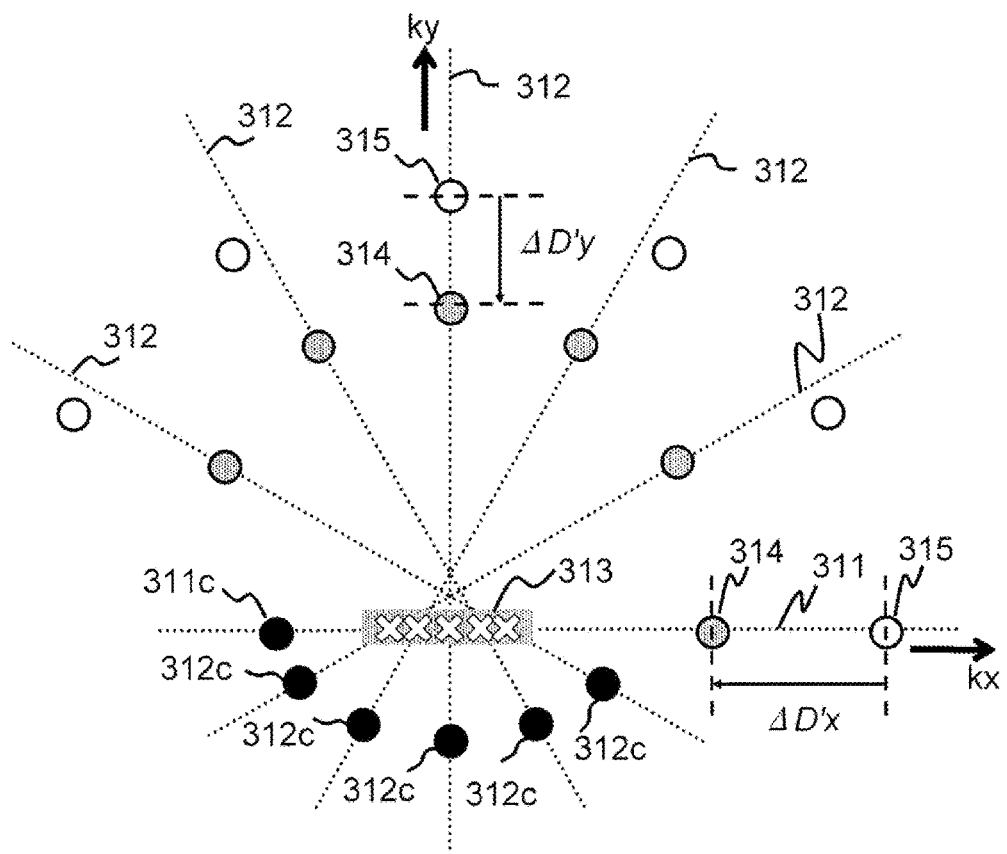
FIG. 5 is a diagram for explaining the phase correction amount calculation method of the first embodiment.

In addition, as shown in FIG. 5, the number of b-th blades 312 is one or more. In addition, when there is a peak shift (shift of the blade center), intersections between the reference blade 311 and the respective b-th blades 312 are not concentrated on one point. For this reason, the phase correction amount calculator 221 calculates the position of the intersection 313 between each b-th blade 312 and the reference blade indicated by a white cross, calculates the distance $\Delta Db1$ to the midpoint 311c of the reference blade 311 and the distance $\Delta Dbb$ to the midpoint 312c of the blade 312 in the above-described procedure, acquires the phase values Phase_1 and Phase_b of the midpoints 311c and 312c, and calculates the phase correction amount PhC_b.

The phase corrector 222 corrects the phases of all the pieces of data, which form the b-th blade 312, using the calculated phase correction amount PhC_b, as described above. In the present embodiment, the phase correction is performed on all the pieces of data forming the b-th blade 312 using the same phase correction amount. That is, a complex data stream Blade_b(x) of the b-th blade 312 after correction is expressed by the following expression (13).

$$\text{Blade\_b}(x)=|\text{Blade\_b}(x)|\cdot\exp(i(\text{PhC\_b})) \quad (13)$$

Here, |Blade_b(x)| indicates the amplitude of the complex data stream of the b-th blade. In addition, i is an imaginary unit.

The reconstructor 223 reconstructs an image using the data stream of each blade after the correction.

Figure 6:
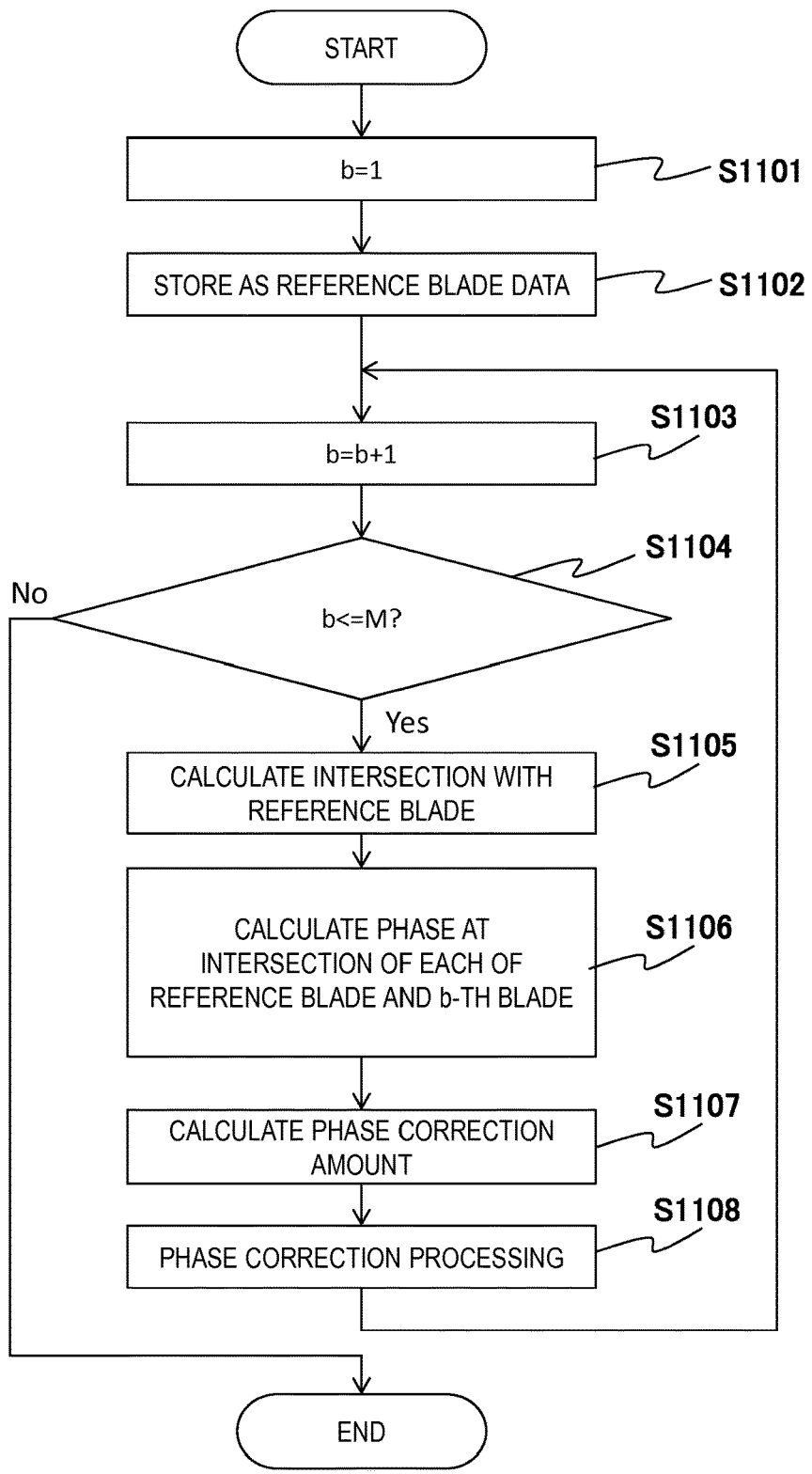
FIG. 6 is a flowchart of the phase correction process in the first embodiment.

Hereinafter, the flow of the phase correction processing by the phase correction amount calculator 221 and the phase corrector 222 of the present embodiment will be described. FIG. 6 is a process flow of the phase correction processing of the present embodiment. Here, a blade acquired first (first blade) is assumed to be the reference blade. b is used as a counter for counting a blade. In addition, the total number of blades is set to M (M is an integer of 1 or more).

The phase correction amount calculator 221 initializes the counter b (b=1) (step S1101). Then, the phase correction amount calculator 221 stores the data stream of the blade acquired by the measurement sector 210 as reference blade data (step S1102). Then, the counter b is incremented by 1 (b=b+1)(step S1103).

The phase correction amount calculator 221 determines whether or not the phase correction processing has ended for all blades (step S1104). Here, it is determined whether or not the counter b exceeds the number of blades M.

When it is determined that the processing has ended for all of the blades 312, the process is ended.

On the other hand, when it is determined that there is the blade 312 that has not been processed, the phase correction amount calculator 221 calculates the coordinates PIb{x, y} of the intersection 313 with the reference blade 311 first for the b-th blade 312 acquired by the measurement sector 210 (step S1105).

Then, the phase correction amount calculator 221 calculates the phase Phase_1 at the intersection 313 of the reference blade 311 and the phase Phase_b at the intersection 313 of the b-th blade 312 (step S1106). Then, the phase correction amount PhC_b of the b-th blade is calculated as a phase difference between both the phases (step S1107).

Then, the phase corrector 222 corrects the phase of the b-th blade according to the above expression (13) using the calculated phase correction amount PhC_b (step S1108). The phase correction amount calculator 221 returns to step S1103 to repeat the processing.

As described above, according to the present embodiment, for the data streams of a plurality of blades acquired according to the non-orthogonal system pulse sequence, the phase correction amount is determined so that the phases at the intersection between the blades match each other, and phase correction is performed. Specifically, a reference blade is determined among the plurality of blades, a phase correction amount is determined so that the phases at the intersections between the reference blade and the other blades match each other, and the phases of all the pieces of data that form each blade are corrected using the phase correction amount. Accordingly, in a place where blades overlap each other, the phase difference is reduced. As a result, the cancellation of signals is reduced. In this case, the phase is corrected using a phase change amount taking into consideration the shift of the center of the received echo of the blade.

In general, in the non-orthogonal sampling method, each blade intersects the reference blade in the low spatial frequency region. Therefore, by matching the phase of each blade at the intersection between the blade and the reference blade with the phase of the reference blade, the phase difference in the low spatial frequency region that affects the image quality most is reduced. This makes it possible to reduce the degradation of image quality.

In the present embodiment, at the time of phase matching at the intersection 313, the phase matching is performed using the interpolation value of only one intersection. However, the present invention is not limited thereto. For example, phase matching may be performed using the average value of the intersection 313 and points thereabout.

Although phase correction is performed in the k-space in the present embodiment, the space to perform the phase correction may be an image space. In the case of performing the phase correction in the image space, the phase correction is performed according to the following expression (14).

$$FT[Blade\_b(x)] = |FT[Blade\_1(x)]| \cdot \exp(i(PhC\_b)) \quad (14)$$

Here, FT[ ] indicates a Fourier transform.

In the present embodiment, as described above, it is necessary to store the data of the reference blade.

In this case, data to be stored may be all pieces of data of the reference blade, or may be data of several points around the origin of the reference blade in order to reduce the memory use.

<<Second Embodiment>>

Next, a second embodiment of the present invention will be described. In the first embodiment, the reference blade is determined, and the phase is corrected so that the phase of each of the other blades at the intersection with the reference blade matches the phase of the reference blade. On the other hand, in the present embodiment, correction is performed so that the phases of the respective blades at an origin offset position POb, which will be described later, match each other. Therefore, in the present embodiment, the setting of the reference blade is not necessary.

An MRI apparatus of the present embodiment has basically the same configuration as the MRI apparatus 100 of the first embodiment. However, the method of calculating the phase correction amount is different as described above. Therefore, the processing of the phase correction amount calculator 221 is different. Hereinafter, the present embodiment will be described focusing on the different configuration from the first embodiment. Also in the present embodiment, according to the pulse sequence of the non-orthogonal sampling method, the measurement sector 210 measures echo signals along a plurality of scanning trajectories of the measurement space (k-space) set in advance, and arranges the echo signals on the scanning trajectories as data streams.

Hereinafter, the phase correction amount calculation processing of the phase correction amount calculator 221 of the present embodiment will be described. In the present embodiment, as in the first embodiment, the phase correction amount is calculated so that the phases of data at a predetermined position on the blades in a plurality of data streams match each other. The predetermined position is the origin offset position that is an intersection of perpendiculars drawn to the plurality of blades from the origin of the k-space, and the phase correction amount calculator 221 calculates the phase correction amount so that all phases of a plurality of data streams at the origin offset position match each other.

The phase correction amount calculator 221 of the present embodiment calculates an offset position using the peak shift amount for each of the plurality of data streams, acquires a distance from the offset position to the midpoint of the data stream using the information of the calculated offset position, and calculates a phase at the offset position of the data stream using the distance.

Also in the present embodiment, as in the first embodiment, the shift amount of the echo signal (peak shift amount) is separately calculated by performing a pre-scan or the like in advance.

Hereinafter, the phase correction amount calculation processing of the phase correction amount calculator 221 of the present embodiment will be described with reference to the diagrams.

FIG. 7(a) shows the positional relationship between a b-th blade 322 and the kx and ky axes in the present embodiment. FIG. 7(b) is an enlarged view of the vicinity of the k-space center in FIG. 7(a).

In the present embodiment, b is an integer of 1 or more. In this diagram, a position 325 indicated by a circle is an ideal data position when there is no positional shift (shift) in the blade 322, and a position 324 indicated by a circle is an actual data position reflecting the shift of the blade 322.

Theoretically, the midpoint (blade center) of each blade 322 is located at an origin 326 of the k-space indicated by a circle. In practice, however, the midpoint (blade center) of each blade 322 is shifted due to the output response of the gradient magnetic field to become a position 322c indicated by a circle.

As described above, an intersection 323 when drawing a perpendicular from the origin of the k-space to the b-th blade 322 is referred to as an origin offset position. In the diagram, the origin offset position is indicated by a white cross. In the present embodiment, the phase of each blade 322 is corrected so that the phases of the respective blades 322 at the origin offset position match each other.

The phase of each blade 322 at the origin offset position 323 is calculated by calculating a distance (error) ΔDb on the k-space between the blade center 322c of each blade 322 and the origin offset position 323. In the present embodiment, the distance ΔDb from the origin offset position 323 on the k-space will be referred to hereinafter as a shift amount in the frequency direction.

Similar to the above expression (3) in the first embodiment, coordinates Pbn of the midpoint (blade center) 322c of each b-th blade 322 are expressed by the following expression (15).

$$Pbn\{x,y\}=\{-\Delta D'x \cos(\theta b), -\Delta D'y \sin(\theta b)\} \quad (15)$$

As in the first embodiment, ΔD'x and Any are shift amounts of each blade in the X-axis direction and the Y-axis direction. θb is an angle between the b-th blade 322 and the X axis.

In addition, the coordinate value {x, y} of the coordinates POb at the origin offset position 323 has the relationship of the following expressions (16) and (17).

$$y+\Delta D'y \sin(\theta b)=\tan(\theta b)\{x+\Delta D'x \cos(\theta b)\} \quad (16)$$

$$y=-x/\tan(\theta b) \quad (17)$$

Therefore, the coordinates POb of the origin offset position 323 are expressed by the following expression (18).

$$POb\{x,y\}=\{\cos(\theta b)\cdot\sin^2(\theta b)\cdot(\Delta D'y-\Delta D'x), \cos^2(\theta b)\cdot\sin(\theta b)\cdot(\Delta D'x-\Delta D'y)\} \quad (18)$$

The shift amount ΔDb of the b-th blade 322 in the frequency direction is calculated as in the following expression (19) from expression (20) using the coordinate position POb of the origin offset position 323 and the coordinates Pbn of the blade center 322c of the b-th blade 322.

$$\Delta Db=\Delta D'x \cos^2(\theta b)+\Delta D'y \sin^2(\theta b) \quad (19)$$

$$\because |\Delta Db|^2=[\cos(\theta b)\cdot\sin^2(\theta b)\cdot(\Delta D'y-\Delta D'x)+\Delta D'x \cos(\theta b)]^2+[\cos^2(\theta b)\cdot\sin(\theta b)\cdot(\Delta D'x-\Delta D'y)+\Delta D'y \sin(\theta b)]^2=(\Delta D'x)^2\cdot\cos^4(\theta b)+2\Delta D'x\cdot\Delta D'y \cos^2(\theta b)\cdot\sin^2(\theta b)+(\Delta D'y)^2\cdot\sin^4(\theta b)=[\Delta D'x \cos^2(\theta b)+\Delta D'y \sin^2(\theta b)]^2 \quad (20)$$

Then, as in the first embodiment, real and imaginary signal values at the calculated origin offset position 323 are acquired by interpolation, and the phase value Phase_b of the b-th blade 322 at the origin offset position 323 is calculated. Phase_b is calculated by the following expression (21).

$$\text{Phase}\_b=\tan^{-1}(\text{Blade}\_b(\text{Imaginary}(\text{CENTER}+\Delta Db))/\text{Blade}\_b(\text{Real}(\text{CENTER}+\Delta Db))) \quad (21)$$

Here, Blade_b( ) indicates a data stream of the b-th blade 322, Real( ) indicates real part data, Imaginary( ) indicates imaginary part data, N indicates the number of data points of each blade, and CENTER indicates the position of the midpoint.

In the present embodiment, the phase values of all blades 322 at the origin offset position 323 are made to match each other. Therefore, for example, assuming that the phase values of all blades 322 at the origin offset position 323 are matched as α [rad], the phase correction amount PhC_b is expressed by the following expression (22).

$$\text{PhC}\_b=\text{Phase}\_b-\alpha \quad (22)$$

For example, 0 is used as α.

By applying the phase correction amount PhC_b to the data stream of the b-th blade 322, the phase values of the respective blades 322 at the origin offset position 323 are matched to each other.

Figure 8:
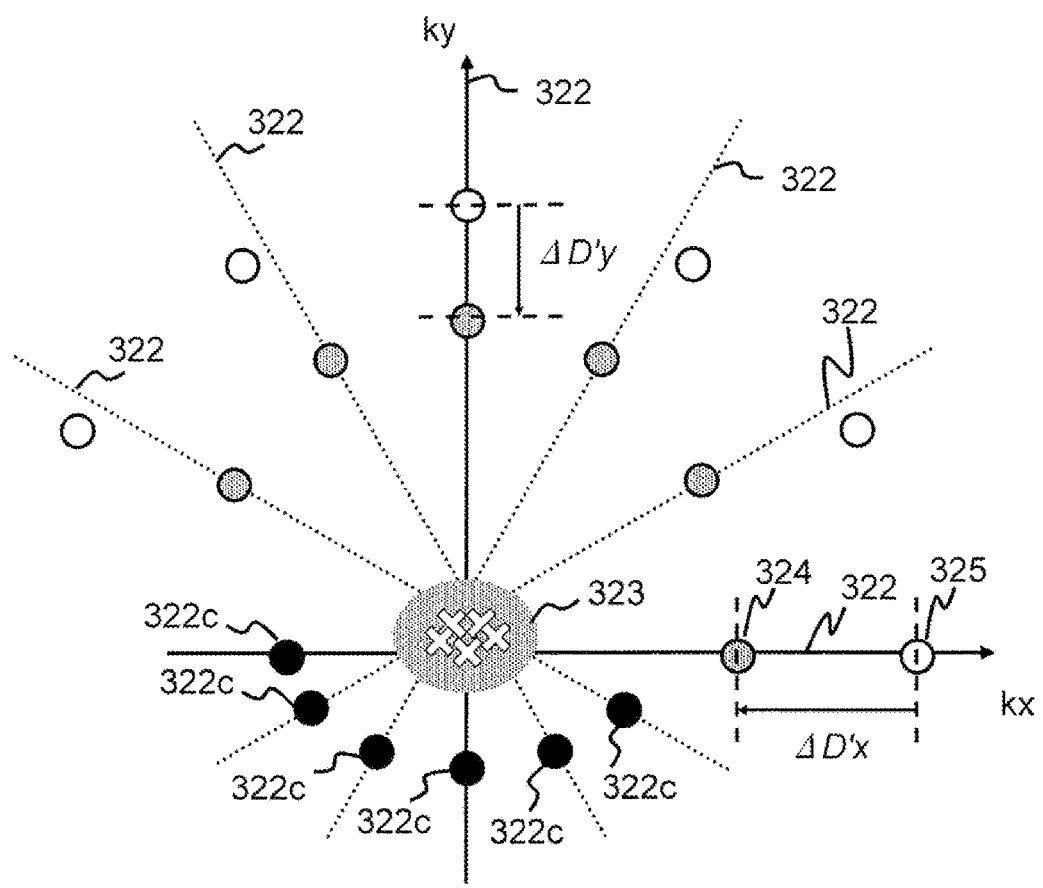
FIG. 8 is a diagram for explaining the phase correction amount calculation method of the second embodiment.

As shown in FIG. 8, a plurality of b-th blades 322 are present. Since there is a shift in the blade center, the origin offset positions 323 of the respective blades 322 are not concentrated on one point. For this reason, also in the present embodiment, the phase correction amount calculator 221 acquires the phase value Phase_b of the origin offset position 323 for each b-th blade, and calculates the position correction amount.

In addition, also in the present embodiment, the phase corrector 222 corrects the phases of all pieces of data, which form the b-th blade 322, using the calculated phase correction amount PhC_b. As in the first embodiment, the complex data stream Blade_b(x) of the b-th blade 322 after correction is expressed by the following expression (23).

$$\text{Blade}\_b(x)=|\text{Blade}\_b(x)|\cdot\exp(i(\text{PhC}\_b)) \quad (23)$$

Here, |Blade_b(x)| indicates the amplitude of the complex data stream of the b-th blade. In addition, i is an imaginary unit.

Figure 9:
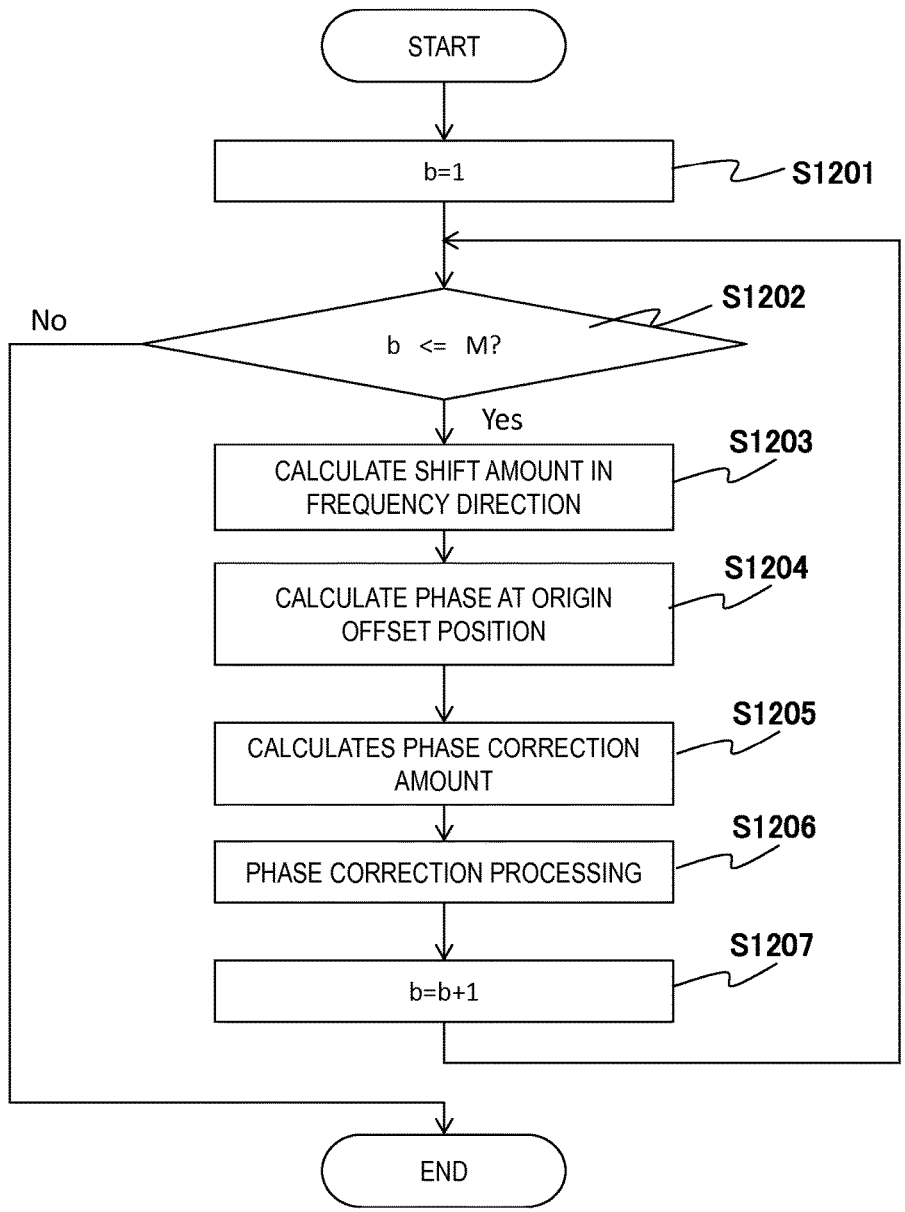
FIG. 9 is a flowchart of the phase correction process in the second embodiment.

Hereinafter, the flow of the phase correction processing by the phase correction amount calculator 221 and the phase corrector 222 of the present embodiment will be described. FIG. 9 is a process flow of the phase correction processing of the present embodiment. b is used as a counter for counting a blade. The total number of blades is set to M (M is an integer of 1 or more).

The phase correction amount calculator 221 initializes the counter b (b=1) (step S1201).

Then, in the present embodiment, the phase correction amount calculator 221 determines whether or not the phase correction processing has ended for all blades (step S1202). Here, it is determined whether or not the counter b exceeds the number of blades M. When it is determined that the processing has ended for all of the blades 312, the process is ended.

On the other hand, when it is determined that there is the blade 322 that has not been processed, the phase correction amount calculator 221 calculates the shift amount ΔDb in the frequency direction for the b-th blade 322 acquired by the measurement sector 210 (step S1203). The phase correction amount calculator 221 calculates a phase at the origin offset position 323 using the calculated shift amount in the frequency direction (step S1204), and calculates the phase correction amount PhC_b of the b-th blade 322 (step S1205).

The phase corrector 222 corrects the b-th blade according to the above expression (23) using the calculated phase correction amount PhC_b (step S1206). The phase correction amount calculator 221 increments the counter b by 1 (step S1207), and returns to step S1202 to repeat the processing.

As described above, according to the present embodiment, for the data streams of a plurality of blades acquired according to the non-orthogonal system pulse sequence, the phase of the data stream of each blade is corrected so that the phases of the respective blades at the origin offset position match each other. Therefore, since a phase shift between blades in the low spatial frequency region is eliminated, it is possible to reduce the signal cancellation that occurs due to the phase shift. Accordingly, it is possible to suppress image quality degradation.

In addition, according to the present embodiment, it is not necessary to select a reference blade. Therefore, it is not necessary to secure a memory region for storing the data of the reference blade. In addition, the phase correction result is not affected by the accuracy of the reference blade.

Also in the present embodiment, as in the first embodiment, phase matching may be performed using the average value of positions around the position 324.

In addition, also in the present embodiment, as in the first embodiment, phase correction may be performed in the image space.

<<Third Embodiment>>

Next, a third embodiment of the present invention will be described. In the present embodiment, from the change in the reception frequency at the time of off-center imaging, the phase value of each blade center is calculated by calculation, and the phase correction amount is determined. In the present embodiment, however, it is assumed that there is no non-uniformity of the static magnetic field and the area error of the gradient magnetic field waveform does not change with time.

An MRI apparatus of the present embodiment has basically the same configuration as the MRI apparatus 100 of the first embodiment. However, the method of calculating the phase correction amount is different as described above. Therefore, the processing of the phase correction amount calculator 221 is different. Hereinafter, the present embodiment will be described focusing on the different configuration from the first embodiment. Also in the present embodiment, according to the pulse sequence of the non-orthogonal sampling method, the measurement sector 210 measures echo signals along a plurality of scanning trajectories of the k-space set in advance, and arranges the echo signals on the scanning trajectories (blades) as data streams. In this case, off-center imaging is performed by changing the reception frequency.

The phase correction amount calculation processing of the phase correction amount calculator 221 of the present embodiment will be described. The phase correction amount calculator 221 of the present embodiment calculates a phase change amount at the midpoint of each of the plurality of data streams using the off-center distance on the k-space, and sets the calculated phase change amount as the phase correction amount. That is, the phase value of the blade center is calculated from the phase change amount during the echo signal acquisition (A/D) at the time of off-center imaging.

When the off-center imaging is performed by shifting the reception frequency on the assumption that there is no non-uniformity of the static magnetic field and the area error of the gradient magnetic field waveform does not change with time, a phase is rotated in each blade due to the shift of the reception frequency. The phase rotation amount can be calculated from the off-center distance, the reception bandwidth, and the field-of-view size. The phase correction amount calculator 221 of the present embodiment sets the calculated phase rotation amount as the phase correction amount. The specific calculation procedure is as follows.

First, a reception frequency Rf at the time of off-center imaging is calculated. The reception frequency Rf is calculated by the following expression (24).

$$Rf = BW \cdot OffcD/FOV \quad (24)$$

Here, BW is a reception frequency band [Hz], OffcD is an off-center distance [m], and FOV is field-of-view size [m].

Figure 10:
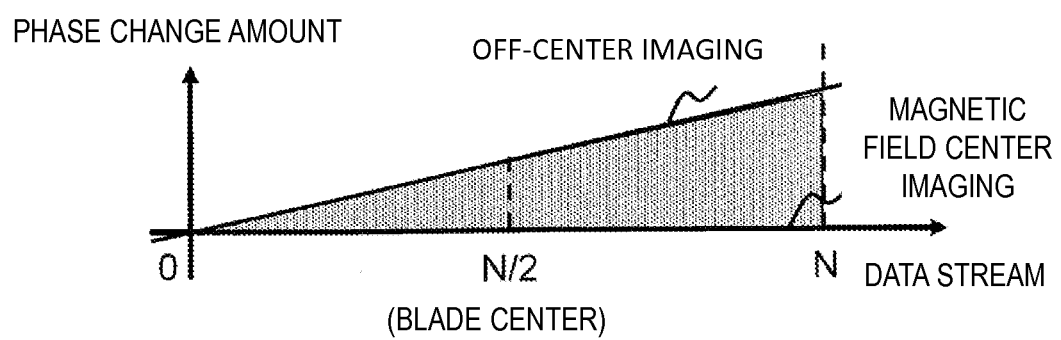
FIG. 10 is a diagram for explaining the phase change amount in a blade in a third embodiment.

In the case of off-center imaging, the phase under detection (A/D) changes as shown in FIG. 10. Therefore, the phase rotation amount (phase change amount) in a blade is expressed by the following formula (25).

$$\Delta\phi f(n) = Rf \cdot \pi \cdot n/BW \quad (25)$$

Here, n is an element number of the data stream that forms a blade.

Therefore, a phase change amount $\Delta\phi x$ in the kx-axis direction of the k-space at the blade center and a phase change amount $\Delta\phi y$ in the ky-axis direction of the k-space at the blade center are expressed by the following expressions (26) and (27), respectively.

$$\Delta\phi x = OffcD\_X/FOV\_X \cdot \pi \cdot CENTER \quad (26)$$

$$\Delta\phi y = OffcD\_Y/FOV\_Y \cdot \pi \cdot CENTER \quad (27)$$

Here, OffcD_X and OffcD_Y are an off-center distance [m] in the X-axis direction and an off-center distance [m] in the Y-axis direction, FOV_X and FOV_Y are a field-of-view size [m] in the X-axis direction and a field-of-view size [m] in the Y-axis direction, and CENTER is a position of the midpoint.

Using this, a phase change amount $\Delta\phi b$ at the b-th blade center is expressed by the following expression (28).

$$\Delta\phi b = \Delta\phi x \cdot \cos(\theta b) - \Delta\phi y \cdot \sin(\theta b) \quad (28)$$

The phase correction amount calculator 221 of the present embodiment calculates the phase change amount $\Delta\phi b$ of each blade at the blade center according to the shift amount of the reception frequency by the above procedure, and determines the phase correction amount PhC_b so that all of the phase change amounts $\Delta\phi b$ are the same. For example, assuming that all phases at the blade centers are $\alpha$ [rad], the phase correction amount PhC_b is expressed by the following expression (29).

$$PhC\_b = \Delta\phi b - \alpha \quad (29)$$

For example, 0 is used as $\alpha$.

Also in the present embodiment, the phases of all pieces of data that form the b-th blade are corrected using the calculated phase correction amount PhC_b. As in the first embodiment, the complex data stream Blade_b(x) of the b-th blade 322 after correction is expressed by the following expression (30).

$$Blade\_b(x) = |Blade\_b(x)| \cdot \exp(i(PhC\_b)) \quad (30)$$

As described above, in the present embodiment, the phase rotation amount of each blade at the blade center is acquired by calculation, and the phase of each blade is corrected so as to reduce the phase difference between blades. This reduces the phase shift between blades. Therefore, it is possible to suppress image quality degradation that occurs due to the phase shift between blades.

Also in the present embodiment, as in the first embodiment, phase correction may be performed in the image space.

In addition, although the peak shift amount of the echo signal is not used in the present embodiment, a peak shift due to non-uniformity of the static magnetic field and the area error of the gradient magnetic field waveform can also be taken into consideration. In this case, phase change amounts $\Delta\phi'x$ and $\Delta\phi'y$ of each blade at the blade center are expressed by the following expressions (31) and (32), respectively.

$$\Delta\phi x = OffcD\_X/FOV\_X \cdot \pi \cdot (CENTER + \Delta D'x) \quad (31)$$

$$\Delta\phi y = OffcD\_Y/FOV\_Y \cdot \pi \cdot (CENTER + \Delta D'y) \quad (32)$$

Therefore, a phase change amount $\Delta\phi'b$ of the b-th blade at the blade center is expressed by the following expression (33).

$$\Delta\phi'b = \Delta\phi'x \cdot \cos(\theta b) - \Delta\phi'y \cdot \sin(\theta b) \qquad (33)$$

When a peak shift is taken into consideration, the phase correction amount PhC_b is determined using the phase change amount $\Delta\phi'b$.

In addition, although the case in which the imaging section is the XY plane of the device coordinate system has been described as an example in each of the above embodiments, the imaging section may be any section. In this case, a peak shift amount at each axis of the device coordinate system is expanded to the measurement coordinate system according to the angle of each blade, and the distances (shift amounts) $\Delta Db1$ and $\Delta Dbb$ from the intersection with the reference blade to the midpoint of each blade are calculated. Specific expansion and calculation methods are as follows.

Coordinates $k_R$ in the measurement coordinate system that reflects the peak shift amount at each of the XYZ axes are expressed by the following expression (34).

$$\begin{aligned} k_R(b, n) &= R_{OM}^T \cdot k_{RA}(b, n) \\ &= \frac{\gamma}{2\pi} \cdot \Delta t \cdot R_{OM}^T \cdot \{(n - Nc)e - d_A\} \cdot R_{OM} \cdot G_{RR}(b) \\ &= \frac{\gamma}{2\pi} \cdot \Delta t \cdot R_{OM}^T \cdot (n - Nc)e \cdot R_{OM} \cdot G_{RR}(b) - \\ &\quad \frac{\gamma}{2\pi} \cdot \Delta t \cdot R_{OM}^T \cdot d_A \cdot R_{OM} \cdot G_{RR}(b) \\ &= \frac{\gamma}{2\pi} \cdot \Delta t \cdot G \cdot [(n - Nc)e - R_{OM}^T \cdot d_A \cdot R_{OM}] \cdot \\ &\quad \begin{bmatrix} 0 \\ \sin\theta b \\ \cos\theta b \end{bmatrix} \end{aligned} \qquad (34)$$

Here, $k_{RA}$ is coordinates in the device coordinate system, $G_{RR}(b1)$ is a read gradient magnetic field [T] at each of the XYZ axes, $d_A$ is a peak shift amount at each of the XYZ axes, b is a blade number, $\theta b$ is a blade angle of a blade (blade b) having a blade number b with respect to the kx axis, n is a data point number in the blade, Nc is a data number of the position of the midpoint, e is a unit matrix, $\gamma$ is a gyromagnetic ratio [rad/T], $\Delta t$ is a sampling interval [s] of the data stream, and G is a gradient magnetic field strength [T]. In addition, $R_{OM}$ is a rotation matrix for transforming the measurement coordinate system into the device coordinate system, and is defined by the following expression (35).

$$R_{OM} = \begin{bmatrix} sx & px & fx \\ sy & py & fy \\ sz & pz & fz \end{bmatrix} \qquad (35)$$

Here, sx, sy, and sz are components of projection of the gradient magnetic field in the slice axis direction in the measurement coordinate system onto the XYZ axes in the device coordinate system, px, py, and pz are components of projection of the gradient magnetic field in the phase encoding axis (ky) direction in the measurement coordinate system onto the XYZ axes in the device coordinate system, and fx, fy, and fz are components of projection of the gradient magnetic field in the read gradient magnetic field axis (kx) direction in the measurement coordinate system onto the XYZ axes in the device coordinate system.

$K_R(b, n)$ in the above expression (34) is the coordinates of the n-th data point of the b-th blade in the measurement coordinate system. This is the same hereinbelow.

Therefore, coordinates $k_S$, $k_P$, and $k_F$ of zero phase encoding data in the measurement coordinate system can be calculated by the following expression (36). Hereinafter, these will be treated as $(\gamma/2\pi) \times \Delta t \times G = 1$ that is standardized.

$$\begin{cases} k_S(b, n) = -\Delta d_S(b) \\ k_P(b, n) = (n - Nc)\sin\theta b - \Delta d_P(b) \\ k_F(b, n) = (n - Nc)\cos\theta b - \Delta d_F(b) \end{cases} \qquad (36)$$

$$\because \begin{cases} \Delta d_F(b) = \Delta d_{FF}\cos\theta b + \Delta d_{FP}\sin\theta b \\ \Delta d_P(b) = \Delta d_{FP}\cos\theta b + \Delta d_{PP}\sin\theta b \\ \Delta d_S(b) = \Delta d_{SF}\cos\theta b + \Delta d_{SP}\sin\theta b \end{cases}$$

$$\begin{cases} \Delta d_{FF} = fx^2 \cdot dx + fy^2 \cdot dy + fz^2 \cdot dz \\ \Delta d_{PP} = px^2 \cdot dx + py^2 \cdot dy + pz^2 \cdot dz \\ \Delta d_{FP} = fx \cdot px \cdot dx + fy \cdot py \cdot dy + fz \cdot pz \cdot dz \\ \Delta d_{SF} = sx \cdot fx \cdot dx + sy \cdot fy \cdot dy + sz \cdot fz \cdot dz \\ \Delta d_{SP} = sx \cdot px \cdot dx + sy \cdot py \cdot dy + sz \cdot pz \cdot dz \end{cases}$$

When arranging blades on a two-dimensional plane ($k_P$ axis-$k_F$ axis plane), the coordinate ($k_S$ axis) in the slice direction does not need to be considered. For this reason, only the $k_P$ and $k_F$ axes will be used hereinafter. The coordinates ($k_F$, $k_P$) of a midpoint $D'_{On}$ (n=Nc) of zero phase encoding in the first blade (b=1) is expressed by the following expression (37).

$$\begin{cases} k_F(l, Nc) = -\Delta d_{FF} \\ k_P(l, Nc) = -\Delta d_{FP} \end{cases} \qquad (37)$$

In addition, the coordinates ($k_F$, $k_P$) of a midpoint $D'_{bn}$ (n=Nc) of zero phase encoding in the b-th blade in the measurement coordinate system is expressed by the following expression (38).

$$\begin{cases} k_F(b, Nc) = -\Delta d_{FF}\cos\theta b - \Delta d_{FP}\sin\theta b \\ k_P(b, Nc) = -\Delta d_{FP}\cos\theta b - \Delta d_{PP}\sin\theta b \end{cases} \qquad (38)$$

Therefore, the expression of the b-th blade in the measurement coordinate system is expressed by the following expression (39), since the inclination is $\tan\theta b$.

$$k_P + \Delta d_{FP}\cos\theta b + \Delta d_{PP}\sin\theta b = \tan\theta b(k_F + \Delta d_{FF}\cos\theta b + \Delta d_{FP}\sin\theta b) \qquad (39)$$

Since the midpoint $D'_{On}$ of the zero phase encoding in the first blade (b=1) is expressed by the above expression (37), the coordinates ($k_F$, $k_P$) of the intersection PIb with the first blade can be calculated by the following expression (40) under the conditions of $\theta b \neq \pi$.

$$\begin{cases} k_F = (\Delta d_{PP} - \Delta d_{FF})\cos\theta b + \Delta d_{FP}\dfrac{(\cos\theta b - 1)\cos\theta b - \sin^2\theta b}{\sin\theta b} \\ k_P = -\Delta d_{FP} \end{cases} \qquad (40)$$

Therefore, the shift amount $\Delta Db1$ of the intersection PIb from the midpoint $D'_{0n}$ of the first blade is expressed by the following expression (41).

$$\Delta Db1 = \Delta d_{FF}(1-\cos\theta b) + \Delta d_{PP}\cos\theta b + \Delta d_{FP}\frac{(\cos\theta b - 1)\cos\theta b - \sin^2\theta b}{\sin\theta b}(\theta b \neq \pi) \quad (41)$$

In addition, the shift amount $|\Delta Dbb|$ of the intersection PIb from the midpoint $D'_{bn}$ of the b-th blade is expressed by the following expression (42).

$$|\Delta Dbb| = \left[\left\{\begin{array}{c}(\Delta d_{PP} - \Delta d_{FF})\cos\theta b + \\ \Delta d_{FP}\frac{(\cos\theta b - 1)\cos\theta b - \sin^2\theta b}{\sin\theta b} + \\ \Delta d_{FF}\cos\theta b + \Delta d_{FP}\sin\theta b\end{array}\right\}^2 + \right.$$
$$\left. \{-\Delta d_{FP} + \Delta d_{FP}\cos\theta b + \Delta d_{PP}\sin\theta b\}^2\right]^{1/2} \quad (42)$$
$$= \left|\Delta d_{PP} + \Delta d_{FP}\frac{\cos\theta b - 1}{\sin\theta b}\right|$$

When the sign is taken into consideration, the shift amount $\Delta Dbb$ of the intersection $I_b$ from the midpoint $D'_{bn}$ of the b-th blade is expressed by the following expression (43).

$$\Delta Dbb = \Delta d_{PP} + \Delta d_{FP}\frac{\cos\theta b - 1}{\sin\theta b}\ (\theta b \neq \pi) \quad (43)$$

Phase correction is performed by calculating the expressions (10) to (13) using the calculated shift amounts $\Delta Db1$ and $\Delta Dbb$ as described above.

In addition, embodiments of the present invention are not limited to the above embodiments. For example, in the embodiments described above, among the non-orthogonal sampling methods, the radial sampling method for radial scanning in the k-space has been illustrated and described as an example. However, a sampling method to be used is not limited thereto. Any sampling method that draws the overlapping trajectories of respective blades on the k-space may be used. For example, a hybrid radial method may be used in which the phase encoding is combined with the radial sampling method.

In the case of the hybrid radial method, the phase correction amount PhC_b is calculated by the method of each of the above embodiments using one trajectory at the center among a plurality of parallel straight trajectories, and the phase of data on all of the plurality of parallel straight trajectories that form one blade is corrected using the phase correction amount PhC_b.

REFERENCE SIGNS LIST

100:MRI apparatus
101:object
120:static magnetic field generation unit
130:gradient magnetic field generation unit
131:gradient magnetic field coil
132:gradient magnetic field power source
140:sequencer
150:high frequency magnetic field generation unit (transmission unit)
151:transmission coil
152:high frequency oscillator
153:modulator
154:high frequency amplifier
160:high frequency magnetic field detection unit (receiving unit)
161:receiving coil
162:signal amplifier
163:quadrature phase detector
164:A/D converter
170:control processing unit
171:CPU
172:storage device
173:display device
174:input device
210:measurement sector
220:image reconstruction sector
221:phase correction amount calculator
222:phase corrector
223:reconstructor
301:blade
301c:blade center
303:position
304:position
305:position
311:reference blade
311c:midpoint
312:blade
312c:midpoint
313:intersection
314:position
315:position
316:origin
322:blade
322c:blade center
323:origin offset position
324:position
325:position
326:origin

The invention claimed is:

1. A magnetic resonance imaging apparatus, comprising:
a measurement sector that measures echoes along a plurality of scanning trajectories in k-space set in advance according to a pulse sequence of a non-orthogonal sampling method and arranges the echoes on the scanning trajectories as data streams; and
an image reconstruction sector that reconstructs an image from the data streams on the plurality of scanning trajectories to obtain a reconstructed image,
wherein the image reconstruction sector includes:
a phase correction amount calculator that calculates a phase correction amount of each of the data streams on the plurality of scanning trajectories;
a phase corrector that corrects a phase of each of the data streams on the plurality of scanning trajectories using the calculated phase correction amount; and
a reconstructor that generates the reconstructed image from the data streams on the plurality of scanning trajectories after the correction, and
the phase correction amount calculator calculates the phase correction amount so as to reduce a phase difference between the data streams on the plurality of scanning trajectories,
wherein the phase correction amount calculator calculates the phase correction amount such that phases of the plurality of scanning trajectories at a predetermined position match each other, and the predetermined position is determined so as to reflect a peak shift amount that is a shift amount of an echo center of the echoes from a k-space origin, and wherein the predetermined position is an intersection between a reference scanning trajectory, which is a scanning trajectory as a reference set in advance among the plurality of scanning trajectories, and each of the other scanning trajectories, and the phase correction amount calculator calculates the phase correction amount such that a phase at the intersection of data streams on the other scanning trajectories match a phase at the intersection of a data stream on the reference scanning trajectory.

2. A magnetic resonance imaging apparatus, comprising:

a measurement sector that measures echoes along a plurality of scanning trajectories in k-space set in advance according to a pulse sequence of a non-orthogonal sampling method and arranges the echoes on the scanning trajectories as data streams; and an image reconstruction sector that reconstructs an image from the data streams on the plurality of scanning trajectories to obtain a reconstructed image, wherein the image reconstruction sector includes:

a phase correction amount calculator that calculates a phase correction amount of each of the data streams on the plurality of scanning trajectories;

a phase corrector that corrects a phase of each of the data streams on the plurality of scanning trajectories using the calculated phase correction amount; and a reconstructor that generates the reconstructed image from the data streams on the plurality of scanning trajectories after the correction, and the phase correction amount calculator calculates the phase correction amount so as to reduce a phase difference between the data streams on the plurality of scanning trajectories, wherein the phase correction amount calculator calculates the phase correction amount such that phases of the plurality of scanning trajectories at a predetermined position match each other, and the predetermined position is determined so as to reflect a peak shift amount that is a shift amount of an echo center of the echoes from a k-space origin, and wherein the predetermined position is an offset position that is an intersection of perpendiculars drawn to the plurality of scanning trajectories from the origin of the k-space, and the phase correction amount calculator calculates the phase correction amount such that all phases of the plurality of data streams at the offset position match each other.

3. The magnetic resonance imaging apparatus according to claim 1, wherein the measurement sector performs off-center imaging, and the phase correction amount calculator calculates a phase change amount at a midpoint of each of the plurality of data streams using an off-center distance on the k-space, and sets the phase change amount as the phase correction amount.

4. The magnetic resonance imaging apparatus according to claim 1, wherein the phase correction amount calculator calculates a position of the intersection using a peak shift amount for each of the data streams on the other scanning trajectories, acquires a distance from the intersection to a midpoint of the data stream and a distance from the intersection to a midpoint of a data stream on the reference scanning trajectory using information of the calculated position of the intersection, and calculates a phase at the intersection of the data stream and a phase at the intersection of the data stream on the reference scanning trajectory using the distances.

5. The magnetic resonance imaging apparatus according to claim 2, wherein the phase correction amount calculator calculates the offset position using the peak shift amount for each of the plurality of data streams, acquires a distance from the offset position to a midpoint of the data stream using information of the calculated offset position, and calculates a phase at the offset position of the data stream using the distance.

6. The magnetic resonance imaging apparatus according to claim 3, wherein the phase correction amount calculator reflects a peak shift amount on the phase change amount at the midpoint of each of the plurality of data streams.

7. The magnetic resonance imaging apparatus according to claim 1, wherein the non-orthogonal sampling method is a radial sampling method or a hybrid radial method.

8. A magnetic resonance imaging method, comprising:

performing phase correction processing for correcting a phase of each of data streams, which are obtained from echoes that are measured along a plurality of scanning trajectories in k-space set in advance according to a pulse sequence of a non-orthogonal sampling method and which are arranged on the scanning trajectories in the k-space, so as to reduce a phase difference in a low spatial frequency region of the k-space between the data streams; and reconstructing an image from echo signals after correction, wherein one of a plurality of the data streams is stored as a reference data stream, and the phase correction processing is performed by calculating an intersection between a scanning trajectory of each of the other data streams and a scanning trajectory of the reference data stream, calculating a phase at the intersection of the data stream and a phase at the intersection of the reference data stream, calculating a phase difference between both phases as a phase correction amount, and correcting a phase of the data stream with the calculated phase correction amount.

9. The magnetic resonance imaging method according to claim 8, wherein the phase correction processing that is performed includes calculating a phase at an offset position of a midpoint of each of a plurality of the data streams, calculating a phase correction amount such that the calculated phase becomes a predetermined value, and correcting the phase of the data stream with the calculated phase correction amount, and the offset position is an intersection position of perpendiculars drawn to the scanning trajectories from an origin of the k-space.

10. The magnetic resonance imaging apparatus according to claim 2, wherein the measurement sector performs off-center imaging, and the phase correction amount calculator calculates a phase change amount at a midpoint of each of the plurality of data streams using an off-center distance on the k-space, and sets the phase change amount as the phase correction amount.

11. The magnetic resonance imaging apparatus according to claim 10, wherein the phase correction amount calculator reflects a peak shift amount on the phase change amount at the midpoint of each of the plurality of data streams.

12. The magnetic resonance imaging apparatus according to claim 2, wherein the non-orthogonal sampling method is a radial sampling method or a hybrid radial method.

\* \* \* \* \*